Figure 1A:
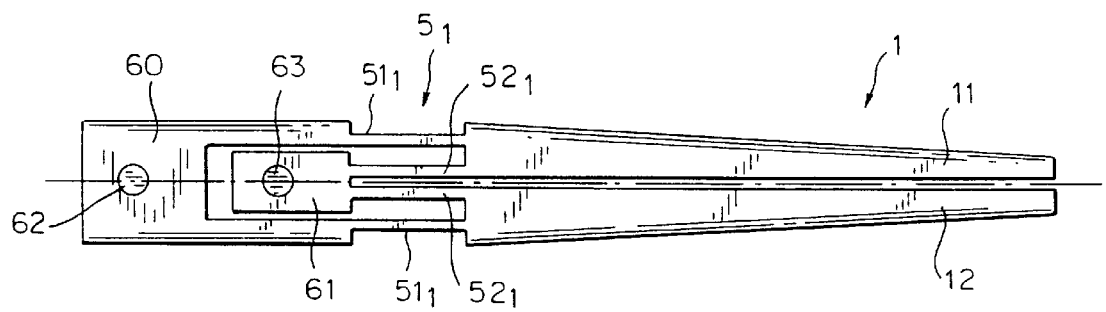

United States Patent [19]
Balazs

[11] Patent Number: 5,964,780
[45] Date of Patent: *Oct. 12, 1999

[54] GRIPPING APPARATUS FOR USE IN MINIMALLY-INVASIVE SURGERY

[75] Inventor: Matthias Balazs, Grafrath, Germany

[73] Assignee: Deutsche Forschungsanstalt fur Luft-und Raumfahrt E.V., Cologne, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/725,909

[22] Filed: Oct. 4, 1996

[30] Foreign Application Priority Data

Oct. 6, 1995 [DE] Germany .............. 195 37 320

[51] Int. Cl.$^6$ ................................. A61B 17/28
[52] U.S. Cl. .................. 606/208; 606/205; 901/31; 901/36; 901/39
[58] Field of Search ................... 606/205, 207, 606/208, 170, 198, 51, 52, 206, 210; 600/564, 565, 218; 294/99.2, 106; 901/31, 39, 36

[56] References Cited

U.S. PATENT DOCUMENTS

| | | | |
|---|---|---|---|
| 3,616,497 | 11/1971 | Esposito | 606/205 X |
| 5,172,700 | 12/1992 | Bencini et al. | 606/207 X |
| 5,339,803 | 8/1994 | Mayzels et al. | |
| 5,353,784 | 10/1994 | Nady-Mohamed | |
| 5,498,256 | 3/1996 | Furnish | 606/208 X |

*Primary Examiner*—Michael H. Thaler
*Attorney, Agent, or Firm*—Browdy and Neimark

[57] ABSTRACT

In an apparatus for operating a robotic device (1), preferably in minimally-invasive surgery and/or robotics, at least one movable robotic part (11; 12) of the robotic device (1) is connected to a first holding part (60) by way of a first, flexible connecting part ($51_1$) of a hinge joint ($5_1$) Moreover, the movable robotic part (11; 12) is connected to a second holding part (61) by way of a second, flexible connecting part ($52_1$) of the hinge joint ($5_1$). This connection is produced in such a way that, when the first holding part (60) moves relative to the second holding part (61) or vice versa, the robotic device (1) pivots the first holding part out of its initial position, and when the part (60 or 61) that has been moved relative to the other part has been brought back, the device restores the part to its initial position.

20 Claims, 7 Drawing Sheets

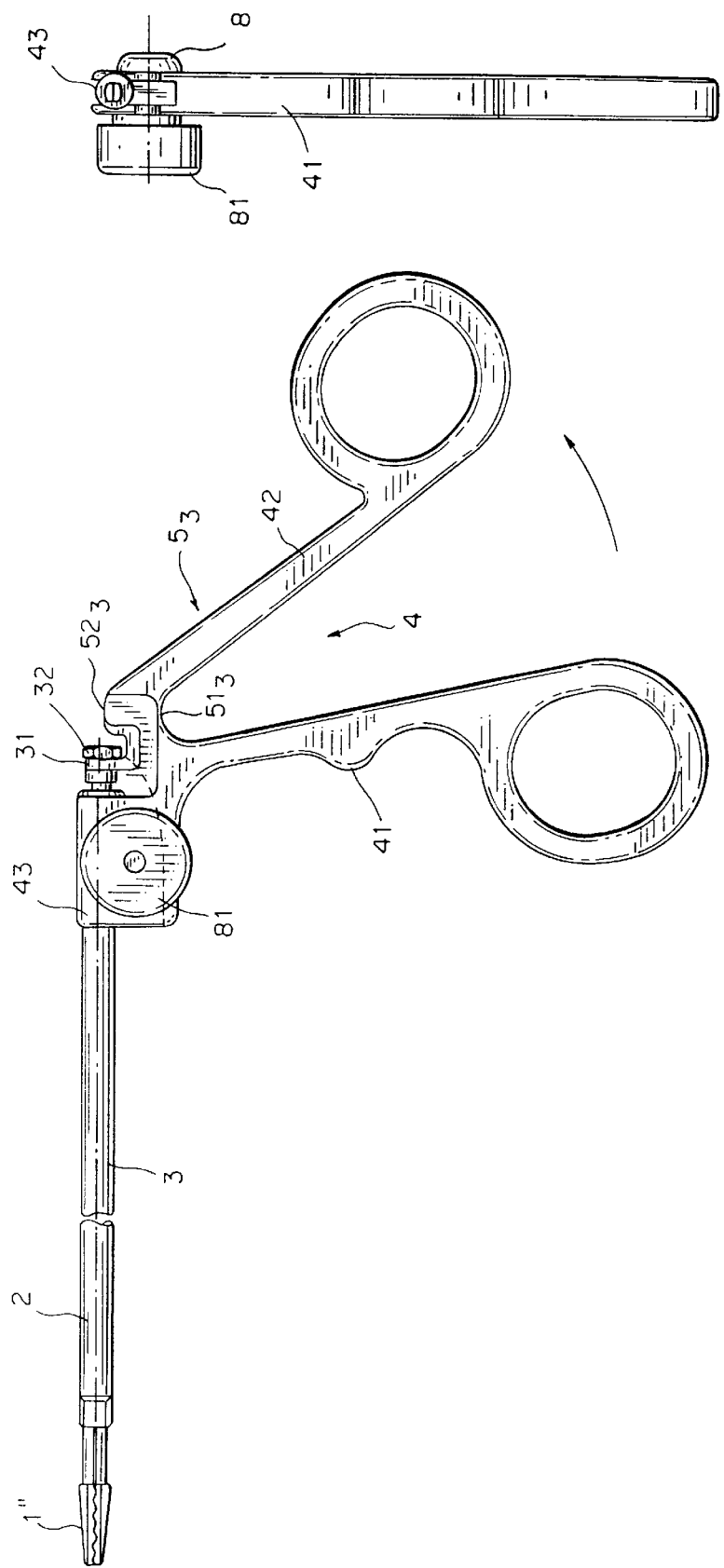

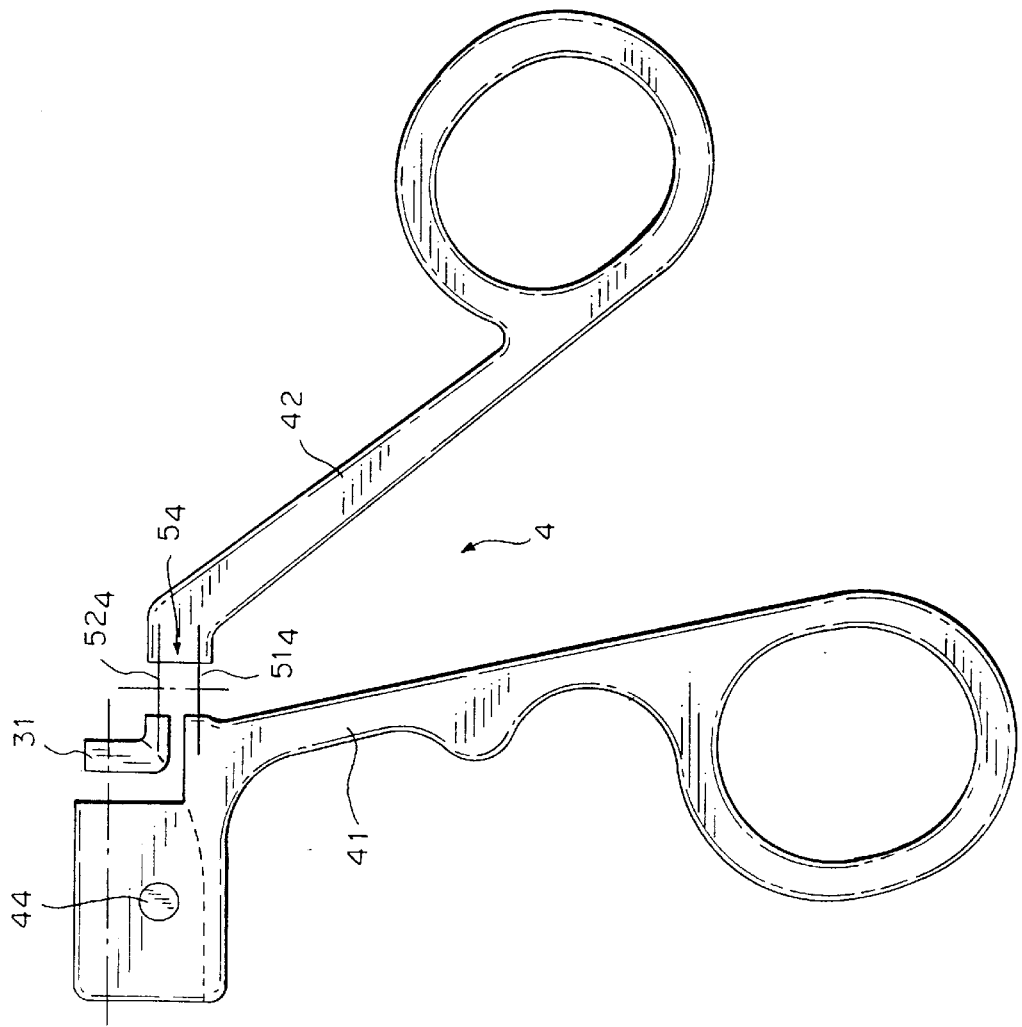

GRIPPING APPARATUS FOR USE IN MINIMALLY-INVASIVE SURGERY

The invention relates to an apparatus for operating a robotic device, preferably in minimally-invasive surgery (MIS) and/or robotics.

In conventional apparatuses for operating robotic devices of this type, such as scissors and forceps, among others, joints are provided which, in the conventional embodiment, are always formed by a plurality, at least two, parts that move toward one another. A relative movement is effected by means of sliding, such as in a pin joint or sled guidance; by rollers, such as in ball bearings and wheels; by tipping, such as in cutting systems as used in beam and scales systems; in bores in ruby bearings, for example of clock gears; by means of transitional members such as chains or belts, for example toothed or V-belts; by means of tappet push rods, as in a valve drive; or by means of slide cams, as in connection with a camshaft, and the like.

In these cases the relative movement always takes place at or in contact points or in contact surfaces. Any relative movement of this nature is, however, necessarily associated with wear, often within a relatively short time, because of the resulting removal or deformation of material. Consequently, in every multiple-part joint, play and friction take place, with the respectively used joint type being a major factor with respect to wear, deformation, play and friction.

The same applies for the mechanics of conventional scissors and forceps used in minimally-invasive surgery. In this case as well, play or stiffness occurs in the respective joints after relatively few sterilization cycles. The resulting wear, in the form of mechanical parts that move counter to one another being worn out and experiencing play, then prevents, for example, precise control of forceps, especially the forceps bit. In addition, gaps and fits result in all conventional joint types, with the disadvantage that these gaps and fits become soiled, and can stick because of soiling and no longer be reliably cleaned and sterilized.

It is therefore an object of the invention to create an apparatus for operating a robotic device that is embodied to be completely free from play and wear.

In accordance with the invention, this is accomplished in an apparatus for operating a robotic device, preferably in minimally-invasive surgery and/or robotics. Moreover, this object is accomplished by an apparatus for operating a robotic device provided at the distal end of an introducer tube, preferably in minimally-invasive surgery, by means of a handle attached by way of connecting means to the proximal end of the introducer tube.

In accordance with the invention a hinge joint is created in which a relative movement is achieved by an elastic deformation, and in special cases also by a plastic deformation. According to the invention, a relative movement consequently occurs between the elements of the hinge joint that move toward or counter to one another.

With the aid of the hinge joint of the invention, a movement is permitted in which a plurality of elements are elastically connected to one another, so that different types of movement kinematics, as well as different additional functions, can be performed with this hinge joint.

In accordance with a preferred refinement of the invention, the structure of the hinge joint can either be produced from a material blank, preferably in the form of a round material blank or tubular blank, or it can be assembled from a plurality of parts.

A preferred refinement of a hinge joint provided at an end effector is an analogous embodiment of the hinge joint in the handle in the same clearance-free and smooth-running hinge structure. If a handle of this type is incorporated into the mechanics, this embodiment constitutes an integrally-closed mechanical system that operates free from clearance and wear and can be used in a preferred manner in minimally-invasive surgery and/or robotics.

In accordance with a further preferred embodiment of the invention, a throughgoing work conduct that extends from the handle to the end effector via the introducer tube is provided in an instrument used in minimally-invasive surgery, for example in the form of forceps, so that the instrument can be expanded by additional functions, such as suction, rinsing, coagulation or the integration of optics, fiber-optical waveguides and/or a laser.

The provision of exclusively elastic joints results in lightweight instrumentation that includes the aforementioned additional functions and can be reliably sterilized. The insertion of an optical fiber and/or a laser into the throughgoing work conduit therefore assures both work and diagnosis with direct viewing-using the robotic device, for example the forceps bit of a forceps serving as an end effector.

If, in accordance with a further preferred embodiment, a forceps bit, for example, can twist without impairment, this provides a further degree of freedom that nevertheless results in minimal play. In both versions, i.e., in the embodiment in which the forceps bit cannot twist, and in the other embodiment, in which it can twist, the forceps can also be very easily disassembled for sterilization and rinsed by means of a pressure connection, for example, and completely sterilized.

Because the hinge joint of the invention can preferably be produced from stainless instrument steel or thermoplastic or rubber-elastic plastics, the hinge joint of the apparatus of the invention for operating robotic devices makes it particularly well-suited for medical applications, and has the advantage over conventional types of joints that no joint gaps are present that art inaccessible to thorough cleaning and therefore sterilization. In many embodiments, therefore, the apparatus of the invention can be cleaned and sterilized without disassembly because of the special embodiment of the hinge joint, because both the connecting parts of the hinge joint, for example, and the work conduits that may be provided for the widely-varying additional functions can easily be rinsed thoroughly.

The apparatus of the invention for operating a robotic device can also be applied in a wide range of fields outside of medical technology, for example in robotics as a primary component of an actuator or in flexible endoscopy, as well as in tests of cavities, for example in the form of grippers having integrated optics.

Moreover, the apparatus of the invention for operating a robotic device can be produced in an extraordinarily cost-effective manner, particularly in mass production, because a plurality of functional elements are elastically connected within a single component, or are assembled from a plurality of components and, at the same time, an expansion is assured by means of additional functions; consequently, a clearance-free—with reference to its lifetime—instrument is created, which can be attributed in particular to the fact that no conventional, mechanical multiple-body joints are provided and used.

Figure 1B:
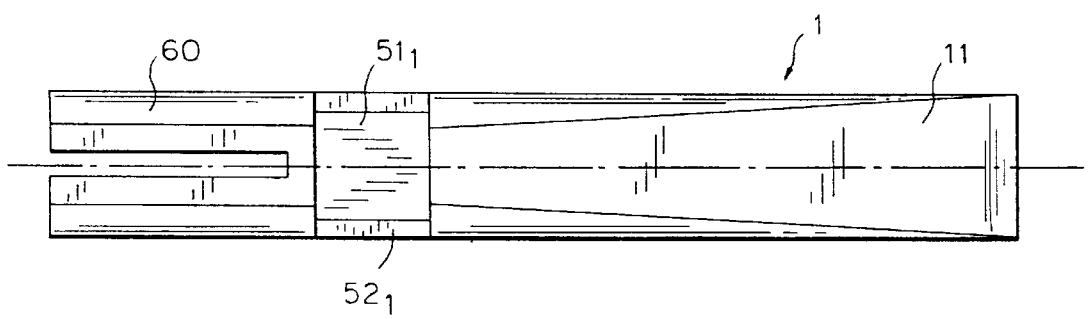
Figure 1C:
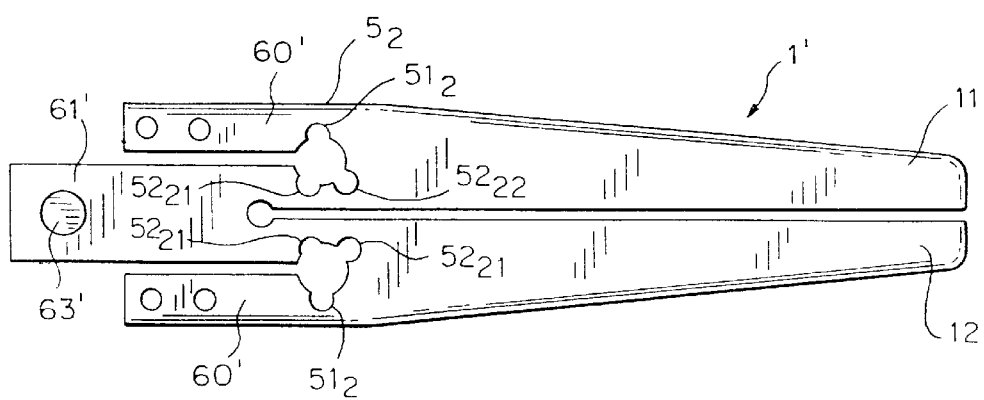
Figure 2A:
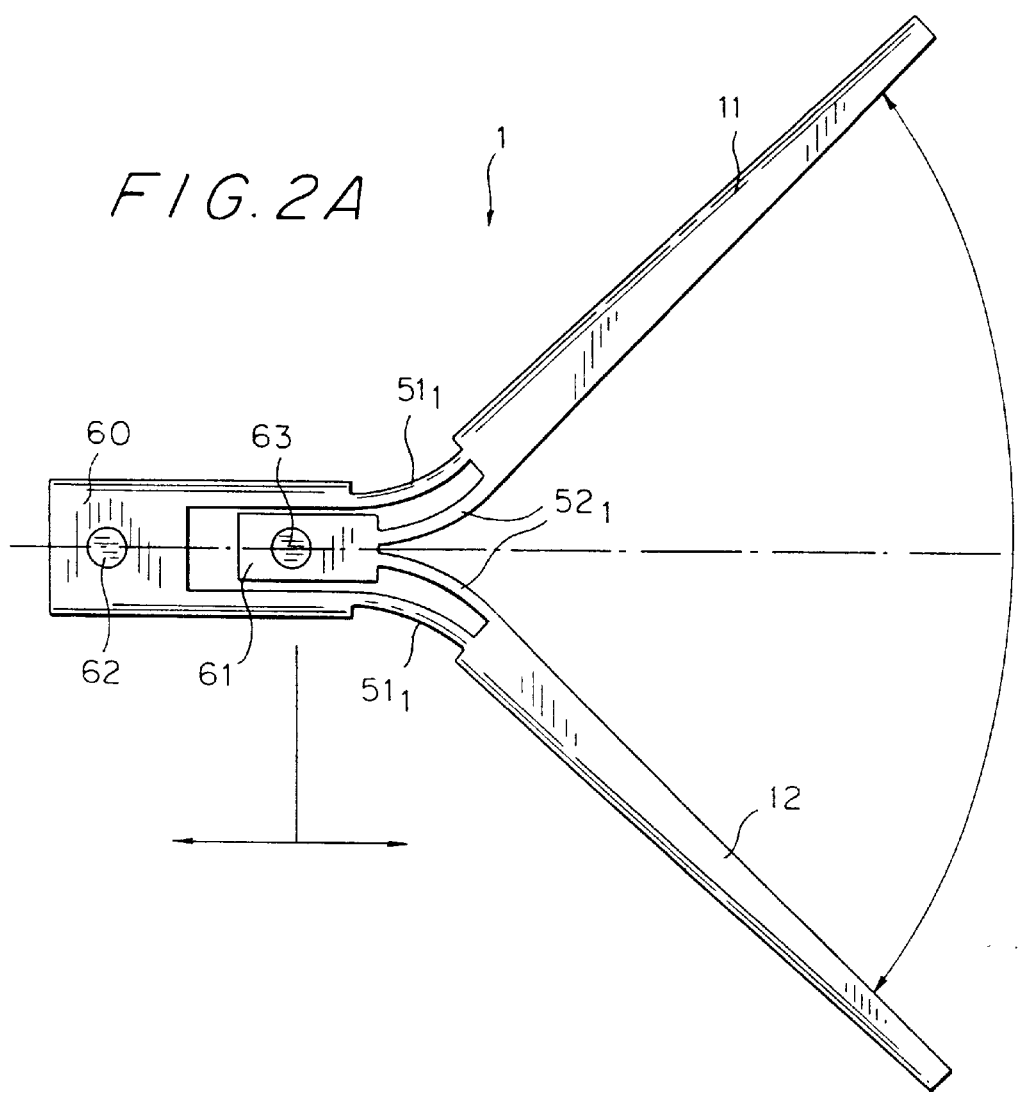
Figure 2B:
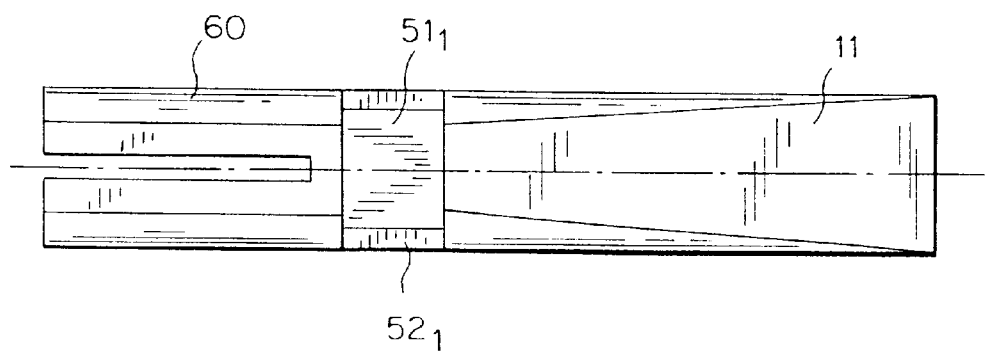
Figure 3A:
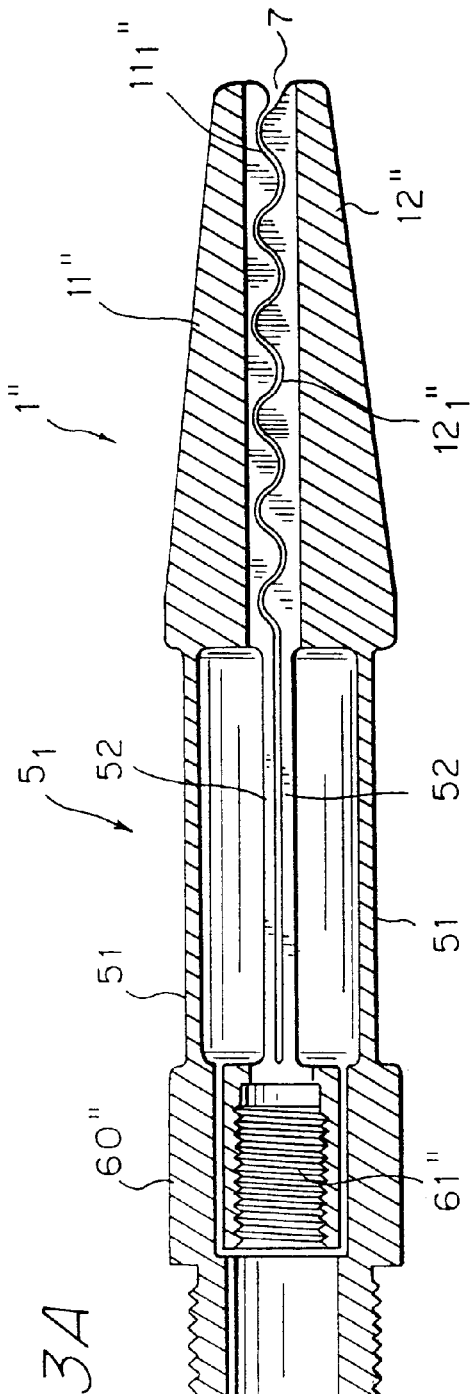
Figure 3B:
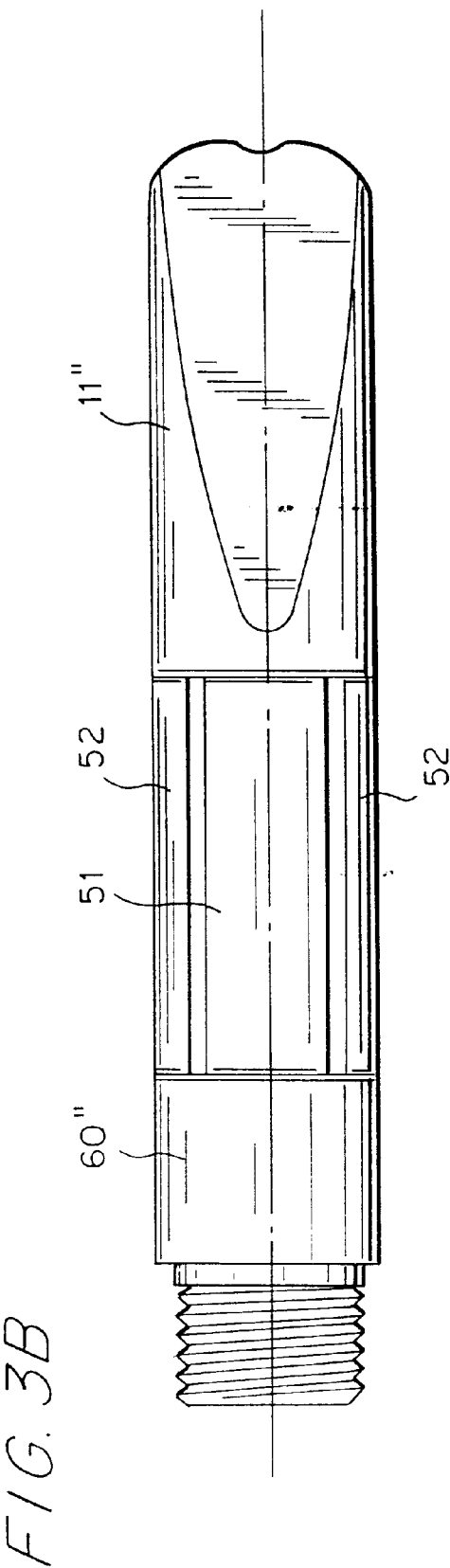
Figure 6:
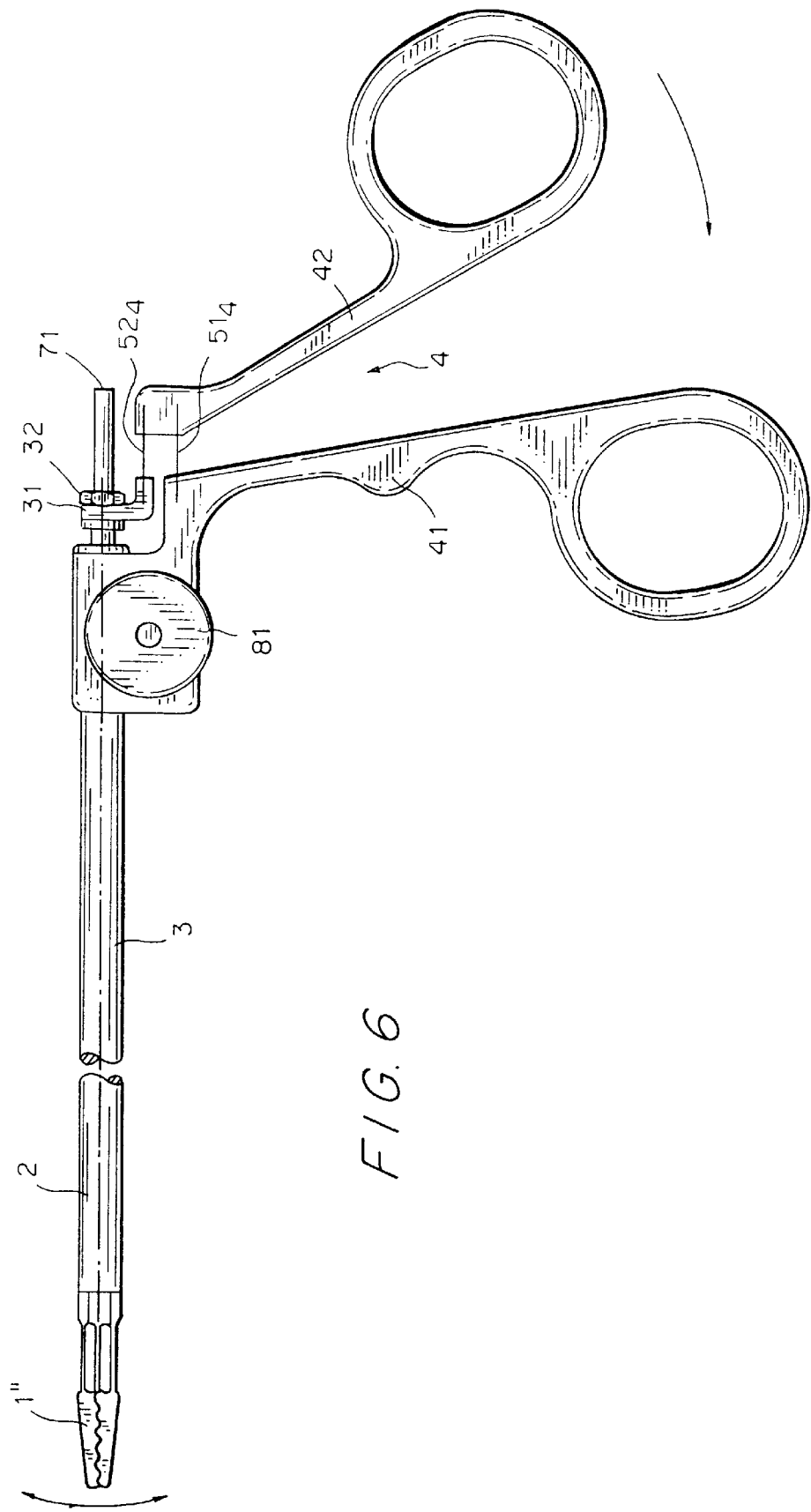
Figure 7:
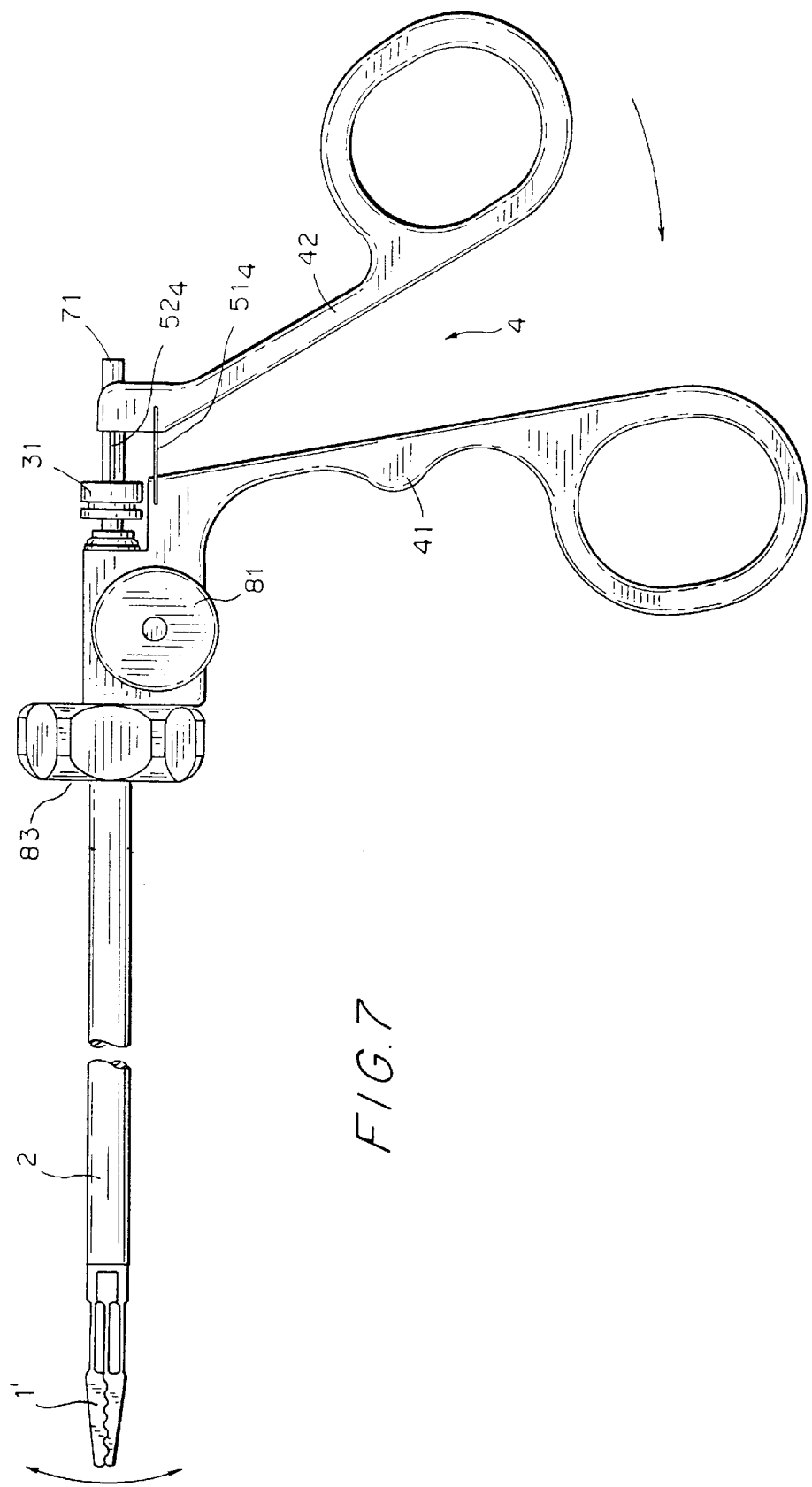

The invention is described in detail below in conjunction with preferred embodiments, with reference to the attached drawings. Shown are in:

FIGS. 1A and 1B schematically, a side and plan view, respectively, of an apparatus for operating a robotic device, shown in the closed state;

FIG. 1c schematically, a side view of an apparatus for operating a robotic device, shown in the closed state and having a hinge joint that is modified with respect to FIGS. 1A and 1B;

FIGS. 2A and 2B also schematically, a side and plan view, respectively, of the apparatus according to FIGS. 1A and 1B, shown in the open state;

FIGS. 3A and 3B also schematically, a sectional and plan view, respectively, of a modification of the apparatus illustrated in FIGS. 1A through 2B, shown in the closed state;

FIGS. 4A and 4B also schematically, a side and plan view, respectively, of an apparatus for operating a robotic device according to FIGS. 1A through 3B, including a handle that is associated with the robotic device;

FIG. 5 a schematic side view of a modification of the handle illustrated in FIG. 4A, including a hinge joint that is modified with respect to FIG. 4A;

FIG. 6 an illustration corresponding to FIG. 4A, with the modified hinge joint illustrated in FIG. 5, and FIG. 7 an illustration corresponding to FIG. 4A, including the modified hinge joint of FIG. 5 and an additional twisting option.

FIGS. 1A and 1B schematically show, in a side and plan view, respectively, an embodiment of an apparatus for operating a robotic device 1 in the closed state. In the illustrated embodiment, the robotic device 1 includes two robotic parts 11 and 12, which can move towards one another. The two robotic parts 11 and 12 are respectively connected to a first holding part 60 by way of a first elastic connecting part $51_1$ of a hinge joint $5_1$. The first holding part 60 is fixedly connected at a location 62 to, for example, an introducer tube (2 in FIGS. 4A and 6) by holding and securing means, not shown in detail.

Furthermore, the movable robotic parts 11 and 12 are respectively connected by way of a second elastic connecting part $52_1$ of the hinge joint $5_1$ to a second holding part 61, which is guided in the first holding part 60 and is displaceable in the direction toward the robotic device 1. A connecting means in the form of a wire can be secured by fastening means, not shown, for example a rivet connection, at a location 63 provided in the second holding part 61; the other end of this connecting means is fixedly connected to, for example, a handle (4 in FIGS. 4A through 6A).

In contrast to FIG. 1A, in FIG. 2A the robotic device 1 is shown in the open state, where, as can be clearly seen in a comparison of the illustrations in FIGS. 1A and 2A, the second holding part 61 is displaced in the direction toward the robotic device 1, i.e., to the right in FIG. 2A. The position that can be inferred from FIG. 1A, in which the inside surfaces of the robotic parts 11 and 12 of the robotic device 1 again rest against one another, is reached by the retraction of the second holding part 61 in the direction toward the fastening location 62 in the first holding part 60, that is, to the left in FIG. 2A.

FIG. 1C shows a sectional view of a modified embodiment of the invention, in which the parts corresponding to those in the embodiment of FIGS. 1A and 1B are provided with the is same reference numerals and an additional apostrophe or, at the connection locations of a hinge joint 5, with subscript numerals 2 and 21, respectively, and 22 instead of the subscript numerals used in FIGS. 1A and 1B.

In contrast to FIG. 1A, FIG. 1C schematically shows a side view of an embodiment of an apparatus for operating a robotic device 1', the embodiment being modified with respect to FIG. 1A and shown in the closed state. The crucial difference between the embodiments is that, at a location 63' in the embodiment of FIG. 1C, the second holding part 61' is fixedly connected to, for example, an introducer tube (2 in FIGS. 4A and 6) by means of holding and fastening means, not shown in detail. In the embodiment of FIG. 1C, the first holding part 60' connected to one of the robotic parts 11 or 12 can move relative to the second holding part 61'.

Furthermore, in contrast to FIGS. 1A and 1B, in FIG. 1C the robotic parts 11 and 12 are respectively connected to the first holding part 60' by way of an elastic connecting part $51_2$, and to the stationary second holding part 61' by way of two connecting locations $52_{21}$ and $52_{22}$, respectively.

During a movement of the first holding part 60' to the left in FIG. 1C, the two robotic parts 11 and 12 are brought into an opened position that corresponds to FIG. 2A. When the first holding parts 60' are brought back into the position shown in FIG. 1C, the two robotic parts 11 and 12 return to the initial, closed position shown in FIG. 1C.

In the embodiment shown in FIGS. 1A through 2B, the first holding part 60 or the first holding parts 60', the second holding part 61 or 61', the flexible connecting parts $51_1$, and $52_1$ of the hinge joint $5_1$, or the flexible connecting locations $51_2$ and $52_{21}$, $52_{22}$ and the two robotic parts 11 or 11' and 12 or 12' of the robotic device 1 or 1' are produced from a material blank, preferably a round material blank, which, unlike in the illustrations in FIGS. 1A through 2B, can have a throughgoing bore for creating a work conduit (for example a work conduit 7 in the embodiment of FIGS. 3A and 3B).

In this instance the material blank can comprise stainless spring steel, a superelastic alloy or thermoplastic and rubber-elastic plastic material. In the use of thermoplastic plastic, quantities of short carbon fibers, glass fibers, contrast materials or electrically-conducting materials can be admixed.

In the use of stainless spring steel, the flexible connecting parts $51_1$ and $52_1$ of the hinge joint $5_1$, which parts are embodied in the form of beams, as well as corresponding connecting surfaces, which are not shown in detail in FIGS. 1A through 2B and are provided for an introduction of force, can be cut out, for example by means of material removal and or erosion.

An embodiment of the apparatus shown in FIGS. 1A through 2B is created by the working out of the second holding part 61 from the blank (with respect to the first holding part 60); in this embodiment, an opening can be achieved by an axial displacement in a direction illustrated by arrows in FIG. 2A, namely by an axial displacement to the right, and a closing of the robotic parts of the robotic device embodied as a forceps can be achieved during a subsequent movement to the left.

Due to and as dictated by an axially-acting slide force, which acts, for example, at the location 63 of the second holding part, a bending moment is exerted on the connecting parts $51_1$ and $52_1$ of the hinge joint $5_1$, across the distance between the two flexible connecting parts $51_1$ and $52_1$, causing these parts to be deformed; consequently, the robotic parts 11 and 12 of the robotic part 1 embodied as a forceps, which parts form the forceps bit in the embodiment according to FIGS. 1A through 2B, are moved in a way that is apparent in a way shown in FIGS. 1A and 2A.

In contrast to the illustrations in FIGS. 1A, 1C and 2A, it is not absolutely necessary to provide two movable robotic parts. An embodiment having only one movable robotic part, for example the robotic part 11, is equally effective; in this instance, unlike in the representations in FIGS. 1A, 1C and 2A, the other robotic part, for example the robotic part 12 in these figures, is fixedly connected to the first holding part in the position that can be inferred from FIG. 1A, or is fixedly connected to the second holding part 61' in the position that can be inferred from FIG. 1C. Because a scissors having, for example, two scissor edges, or a gripper having a plurality of gripper arms can be moved in place of the robotic device 1 in the form of a forceps, embodiments that include multiple-arm robotic devices can be moved, that is, pivoted in the way that can be inferred from FIGS. 1A and 2A.

FIGS. 3A and 3B show, in a sectional and plan view, respectively, a second modified embodiment of the invention in which the parts corresponding to those in the embodiment in FIGS. 1A through 2B are provided with the same reference numerals and two additional apostrophes.

The crucial difference between the second modified embodiment in FIGS. 3A and 3B and the other two embodiments is that screw connections are provided in order to connect operating elements, that is, an inner thread is embodied at the second holding part 61", and an outer thread is embodied at the first holding part 60"; a work conduit 7 is embodied symmetrically to an axis of symmetry, indicated in dashed lines, in the robotic device 1", in other words, in its robotic parts 11" and 12", as well as between the connecting parts $52_1$ of the hinge joint $5_1$, the second holding part 61" and the first holding part 60".

Furthermore, the gripping surfaces that have been optimized for tissue, that is, the outside regions of the robotic parts 11" and 12" of the robotic device 1", are uniformly corrugated (as uniformly corrugated edge regions $11_1$" and $12_1$" in the way that can be inferred from the sectional view of FIG. 3A).

FIGS. 4A and 4B show a plan and frontal view, respectively, of an apparatus for operating a robotic device 1" attached to the distal end of an introducer tube 2 (see FIG. 3A). In this instance, a handle 4 is provided that is connected by way of a connecting means, not shown, for example in the form of a tube or a pushing wire 3 guided in the handle, to the robotic device 1" provided at the distal end.

The handle 4 has a first grip part 41, in the upper part of which a conduit 43 that is open to the top is embodied, as can be seen from the frontal view of FIG. 4B. The grip part 41 is fixedly connected, by means of a screw 8 and a knurled nut 81 screwed onto it, to the distal end of the introducer tube 2 inserted into the open conduit 43. A second grip part 42 is connected to the first grip part 41 by way of an elastic connecting part $51_3$ of a hinge joint $5_3$. A holding and fastening part 31 is connected to the second grip part 42 by way of a second, elastic connecting part $52_3$ of the hinge joint $5_3$. The connecting means, in the form of a tube or a pushing wire 3, is secured to the holding and fastening part 31 by way of corresponding fastening elements, of which only a holding nut 32 is shown in FIG. 4A.

By means of an elastic bending of the two connecting parts $51_3$ and $52_3$ of the hinge joint $5_3$, the robotic device 1', in the form of a forceps, is brought into an opened state that corresponds to FIG. 2A (which clearly shows that the elastic bending of the connecting parts includes bending over their full lengths) by means of a pivoting of the grip part 42 in the direction indicated by an arrow in FIG. 4A. A pivoting of the grip part 42 in a direction counter to the arrow direction in FIG. 4A then allows the robotic device 1' to be brought back into the closed state that can be inferred from FIG. 4A, for example.

The schematic side view of FIG. 5 only shows the handle 4, which is modified in that the elastic connecting parts $51_3$ and $52_3$ of the hinge joint $5_3$ which are provided in the embodiment according to FIG. 4A and comprise the same material as the grip parts 41 and 42, are replaced by connecting parts $51_4$ and $52_4$ of the hinge joint $5_4$ comprising spring steel. Here one end of the spring-steel connecting part $51_4$ is inserted into the grip part 41, and its other end is inserted into the grip part 42, while one end of the second spring-steel connecting part $52_4$ is inserted into the holding and fastening part 31 and its other end is inserted into the second grip part $52_1$ above the connecting part $51_4$ in the plan view of FIG. 5.

FIG. 6 shows a side view of a further embodiment of the apparatus of the invention; this embodiment differs from the embodiment shown in FIG. 4A in that, in the embodiment in FIG. 6, the handle shown in FIG. 5 is attached to the distal end of the introducer tube 2. Here, as illustrated in connection with FIG. 5, the two grip parts 41 and 42 of the handle 4, or the grip part 42 and the holding and fastening part 31, are elastically connected to one another by connecting elements $51_4$ and $52_4$, preferably of spring steel. Furthermore, a shoulder 71 is provided at the work conduit 7 in FIG. 6.

The spring-steel connecting parts $51_4$ and $52_4$ provided in the embodiments of FIGS. 5 and 6 can also replace the connecting parts $51_1$ through $51_3$ and $52_1$ through $52_3$ provided in the embodiments in FIGS. 1A through 4A, which are produced from the same material as the robotic parts of the robotic device 1 or 1'.

The embodiment illustrated in FIG. 7 is distinguished from the embodiment of FIG. 6 in that the introducer tube 2 can additionally be twisted by means of a part attached to its proximal end.

With the aid of the hinge joint $5_1$ through $5_4$ of the invention, having connecting parts $51_1$ through $51_4$ and $52_1$ through $52_4$, the forms of movement can be established predominantly by a variation in the following dimensions or points:

length, thickness, width, spacing and angle of connecting pieces (disposed parallel in the example);

planar or spatial arrangement of the elements;

symmetry or asymmetry of the connecting pieces;

selection of the stationary or displaceable coupling surface;

path of movement of the displaceable coupling surfaces:
 linear movement (along a straight line);
 circular movement (for example along a circle segment);
 arbitrary movement, for example on a planar or spatial path of the displaceable coupling surface that has been predetermined by a robot.

Moreover, an apparatus for operating a robotic device, preferably in minimally-invasive surgery and/or robotics, having the hinge joint of the invention, can be realized not only in a planar arrangement, but can also be embodied as a spatial joint. Consequently, almost any arbitrary forms of movement are possible, namely a tangential bend with a gently-curving line in one direction in the plane;

a tangential bend with a gently-curving line in two directions in the plane;

a tangential bend with a gently-curving line in arbitrary predominant directions in space;

rotation about an axis;

shortening or lengthening in one axis direction;

spiral-shaped twisting about an axis;

spiral-shaped twisting about an axis with superpositioning of curving;

further possible combinations of these basic types, with the outer shape of the hinge joint permitting arbitrary cross-sectional courses.

The apparatus of the invention for operating a robotic device can also be produced from semi-products having arbitrary geometries, preferably from oblong semi-products having a rectangular cross section;

oblong semi-products having a circular or ellipsoidal cross section;

oblong semi-products having arbitrary polygonal cross sections;

oblong semi-products having arbitrary hollow cross sections, preferably tubes, and technical profiles;

half-semi-products having arbitrary cross-sectional shapes (for example the above-described examples) or having arbitrary cross-sectional courses over the length of a component that is preferably embodied to be conical, cuneiform, or to have arbitrary, continuous or noncontinuous cross-sectional courses, for example a rectangular cross section that changes over continuously into an ellipsoidal cross section.

Arbitrary, passive additional functions can be integrated into the apparatus of the invention for operating a robotic device, preferably in minimally-invasive surgery and/or robotics, by means of corresponding shaping of the components, preferably suction and rinsing conduits, conduits for receiving drives for instruments or devices that must be actuated through the apparatus for operating a robotic device, preferably actively-controllable optics;

cable conduits for the insulated supply of a high-frequency current for coagulation.

Furthermore, the apparatus for operating a robotic device according to the invention can be moved by means of arbitrary drives, particularly by means of clearance-free, low-friction drives which are operated manually, for example, or by means of electromotive, hydraulic or pneumatic drives, piezoactuators or similar control members.

I claim:

1. An apparatus for use in minimally-invasive surgery, comprising a gripping device (1, 1', 1") including holding parts (60, 60', 60", 61, 61', 61") including a first holding part and a second holding part and movable gripping parts (11, 11', 11"; 12, 12', 12"), each gripping part being connected by way of a respective first, outer, flexible beam ($51_1$ through $51_4$) of a hinge joint ($5_1$ through $5_4$) to the first holding part (60, 60', 60") and by a respective second, inner flexible beam ($52_1$ through $52_4$) to the second holding part (61, 61', 61");

wherein the first beam and the second beam are approximately equal in length, and wherein each of the first beam and the second beam is flexible along substantially an entire length thereof;

whereby, when one of the holding parts (60, 60', 60", 61, 61', 61") moves relative to another of the holding parts, the gripping device (1, 1', 1") is pivoted out of its initial position and is opened and, when the first holding part (60, 60'or 61, 61') that has moved relative to the second holding part (61, 61'or 60, 60') is brought back, the gripping device is closed in such a way that inner surfaces of the gripping parts (11, 11', 11"; 12, 12', 12") are adjacent.

2. The apparatus according to claim 1, characterized in that the gripping device (1") comprises a throughgoing, tubular work conduit (7), the work conduit including an axis thereof.

3. The apparatus according to claim 2, characterized in that the first holding part (60, 60', 60"), the second holding part (61, 61', 61"), the flexible first beam and second beam ($51_1$ through $51_3$; $52_1$ through $52_3$) of the hinge joint ($5_1$ through $5_3$) and the gripping parts (11, 11', 11"; 12, 12', 12") of the gripping device (1, 1', 1") are produced from just one material bank.

4. The apparatus according to claim 3, characterized in that the material blank is a round or tubular material blank.

5. The apparatus according to claim 4, characterized in that the material blank is stainless spring steel.

6. The apparatus according to claim 4, characterized in that the material blank comprises a superelastic alloy.

7. The apparatus according to claim 4, characterized in that the material blank comprises a thermoplastic or rubber-elastic plastic material.

8. The apparatus according to claim 7, characterized in that the thermoplastic contains admixtures of short carbon fibers, glass fibers, contrast materials or electrically-conducting materials.

9. The apparatus according to claim 4, characterized in that the two grip parts (41, 42) of the handle (4) are produced from materials which include aluminum, stainless instrument steel, stainless spring steel, thermoplastic plastic or rubber-elastic plastic, with or without admixtures, and the two first beam and second beam ($51_4$, $52_4$) of the hinge joint ($5_4$) comprise stainless spring steel.

10. The apparatus according to claim 3, characterized in that the material blank comprises a round or tubular material blank.

11. The apparatus according to claim 10, characterized in that first holding part(60, 60', 60"), second holding part (61, 61', 61") and the gripping device (1, 1', 1") include aluminum, stainless instrument steel, stainless spring steel, thermoplastic plastic or rubber-elastic plastic, with or without admixtures, and the flexible connecting parts of the hinge joint are formed from stainless spring steel.

12. The apparatus according to claim 3, characterized in that the material blank comprises stainless spring steel.

13. The apparatus according to claim 3, characterized in that the material blank comprises a superelastic alloy.

14. The apparatus according to claim 3, characterized in that the material blank comprises a thermoplastic or rubber-elastic plastic material.

15. The apparatus according to claim 2, characterized in that first holding part (60, 60', 60"), second holding parts (61, 61', 61") and the gripping device (1, 1', 1") include aluminum, stainless instrument steel, stainless spring steel, thermoplastic plastic or rubber-elastic plastic, with or without admixtures, and the flexible connecting parts of the hinge joint are formed from stainless spring steel.

16. The apparatus according to claim 1 comprising an introducer tube, the device being provided at a distal end of the introducer tube (2), and a handle (4), including a first grip part (41) and a second grip part (42), wherein the first grip part (41) of the handle (4) is attached to a proximal end of the introducer tube (2), and the second grip part (42) is connected to the first grip part (41), wherein a connecting means (3) couples the second grip part to the gripping device (1") in such a way that the gripping device (1") can be operated by a movement of the second grip part (42) relative to the first grip part (41) by way of the connecting means (3).

17. The apparatus according to claim 16, characterized in that the handle (4; 41, 42) having the hinge joint ($5_3$; $51_3$, $52_3$) is produced from one material blank.

18. The apparatus according to claim 1, characterized in that first holding part (60, 60', 60"), second holding part (61, 61', 61") and the gripping device include aluminum, stainless instrument steel, stainless spring steel, thermoplastic plastic or rubber-elastic plastic, with or without admixtures, and the flexible connecting parts of the hinge joint are formed from stainless spring steel.

19. The apparatus according to claim 1, characterized in that the first holding part (60, 60', 60"), the second holding part (61, 61', 61"), the flexible connecting parts (51$_1$, through 51$_3$; 52$_1$ through 52$_3$) of the hinge joint (51 through 53) and the gripping part (11, 11', 11"; 12, 12', 12") of the gripping device (1, 1', 1") are produced from a single material blank.

20. The apparatus according to claim 19, characterized in that the material blank comprises a round or tubular material blank.

* * * * *